United States Patent [19]

Wu et al.

[11] 4,274,832
[45] Jun. 23, 1981

[54] ANALYTICAL ELEMENT AND METHOD FOR ANALYSIS OF MULTIPLE ANALYTES

[75] Inventors: Tai-Wing Wu, Rochester; Glen M. Dappen, Webster, both of N.Y.

[73] Assignee: Eastman Kodak Company, Rochester, N.Y.

[21] Appl. No.: 11,605

[22] Filed: Feb. 12, 1979

[51] Int. Cl.$^3$ .................... G01N 33/00; G01N 33/52; G01N 33/72; G01N 33/92
[52] U.S. Cl. ............................... 23/230 R; 23/230 B; 23/905; 23/909; 422/56; 435/4; 435/11; 435/14; 435/18; 435/805
[58] Field of Search ............ 23/230 B, 230.3, 230 R, 23/905, 909; 422/55–57; 435/11, 14, 18, 4, 805, 810

[56] References Cited

U.S. PATENT DOCUMENTS

| Re. 28,339 | 2/1975 | Maxon | 23/230 R X |
|---|---|---|---|
| 3,001,915 | 9/1961 | Fonner | 42/56 |
| 3,992,158 | 11/1976 | Przybylowicz et al. | 422/57 |
| 4,038,485 | 7/1977 | Johnston et al. | 435/11 X |
| 4,042,335 | 8/1977 | Clement | 422/56 |
| 4,066,403 | 1/1978 | Bruschi | 23/230 B |
| 4,069,016 | 1/1978 | Wu | 23/230 B |
| 4,069,017 | 1/1978 | Wu et al. | 23/230 B |
| 4,129,417 | 12/1978 | White | 435/18 X |
| 4,160,008 | 7/1979 | Fenocketti et al. | 422/56 |

FOREIGN PATENT DOCUMENTS

| 2347111 | 3/1975 | Fed. Rep. of Germany . | |
| 6815866 | 5/1970 | Netherlands | 422/56 |

*Primary Examiner*—Arnold Turk
*Attorney, Agent, or Firm*—J. Jeffrey Hawley

[57] ABSTRACT

An analytical element for the detection of two or more analytes in an aqueous liquid. The element contains an essentially dry matrix, at least a portion of the matrix containing at least two interactive compositions, a first composition generating a first radiometrically detectable species corresponding to the presence and/or concentration of one analyte, and a second composition for the inhibition or the destruction of a second radiometrically detectable species corresponding to the presence and/or concentration of one of the other analytes. The first and second interactive compositions are positioned in the element matrix to be in liquid contact with one another. Each of the first and second detectable species produced in the element is selected to have a different, characteristic, detectable absorption or emission peak in the electromagnetic spectrum.

17 Claims, No Drawings

ANALYTICAL ELEMENT AND METHOD FOR ANALYSIS OF MULTIPLE ANALYTES

FIELD OF THE INVENTION

The present invention relates to an analytical element for the analysis of at least two substances, hereinafter referred to as analytes, contained in a liquid sample. These analytical elements are particularly useful in the "dry chemistry" analysis of aqueous liquids. "Dry chemistry" refers to analytical methods and techniques in which analysis is carried out using chemical reagents, sometimes termed interactive compositions, contained in "dry-to-the-touch" elements such as "dip-and-read" test strips, multilayer test elements and the like.

BACKGROUND OF THE INVENTION

An increasingly large number of analytical analyses (i.e., assays) must be performed each day on many kinds of liquid samples, including, but not limited to, aqueous biological fluids such as blood, serum, urine, cerebral spinal fluid, and the like. To expedite the handling of these assays in the analytical laboratory, "dry chemistry" analytical elements have been proposed which are capable of analyzing for two or more analytes contained in a liquid sample. The utility of such an element is self evident. If a single analytical element can provide an assay for two or more analytes in a liquid sample, the number of test elements and/or liquid samples needed to conduct a complete analysis of the liquid can be substantially reduced. Moreover, if the assays can be conducted simultaneously, analysis time is likewise reduced.

Various "dry chemistry" analytical elements have been developed wherein a single test element is capable of multiple analyte detection. For example, U.S. Pat. No. 3,001,915 issued Sept. 26, 1961 and U.S. Pat. No. Re. 28,339, issued Feb. 18, 1975 each disclose a "dry chemistry" test element having the capability of detecting two or more analytes contained in a sample of test liquid. The dry test elements described in each of these patents provide multiple analyte detection by having a different interactive compositions for each of the analytes to be detected contained in a separate zone of the elements, the zones being longitudinally spaced along the length of the element. Each of the individual interactive compositions remains separated from one another upon application of the liquid test sample to the element and liquid contact among individual interactive compositions within the element is prevented. In use, a liquid sample applied to the element provides a measure of the concentration of each analyte in the sample by, for example, a separate color change occurring in each zone upon reaction of each interactive composition with the sample.

Another type of "dry chemistry" analytical element having multiple analyte detection capability is disclosed in West German patent-of-addition No. 2,347,111 published Mar. 27, 1975. This patent-of-addition discloses a single test strip having, in separate portions of the strip, individual precipitation reagent compositions, each of which is capable of analyzing for a different analyte of a liquid sample. In use, a liquid sample applied to this test strip simultaneously contacts each of the different portions of the test strip. A different precipitate thus forms in each portion of the test strip in response to the particular analyte for which the reagent contained in that portion is sensitive. The pattern of light scattering produced by the attenuation of a light beam directed at the precipitate formation in each portion of the test strip is then used as a measure to determine the presence and/or concentration of the individual analytes contained in the liquid sample. Although each of the different reagent compositions of the test strip disclosed in West German patent-of-addition No. 2,347,111 is located in a distinct portion of the strip, typically with a physical gap therebetween, liquid contact between these individual reagent compositions apparently can occur.

Liquid contact occurring among the individual reagent compositions of a test element for multiple analyte detection can present a real problem. One is faced with the problem of preventing detection signal interference, i.e., preventing interference between a detectable signal generated by one reagent composition upon interaction with one of the analytes and a separate signal produced upon interaction of a second reagent composition with one of the other analytes.

This interference problem is particularly acute where analyte presence and/or concentration is detected by conventional radiometric detection techniques. These techniques rely upon changes in the absorption spectrum of a reference light beam transmitted through or reflected from the element or upon changes in the emission spectrum of the element in response to such a reference light beam. This is because one must distinguish between possible overlapping absorption or emission bands if the interactive product(s) of one analyte reaction come into fluid contact with the interactive product(s) of another analyte.

To alleviate this interference problem, the analytical elements described in the aforementioned U.S. Pat. Nos. 3,001,915 and Re. 28,339 employ special barrier means or compositions to completely prevent the occurrence of fluid contact among individual interactive compositions. In West German patent-of-addition No. 2,347,111 the problem is apparently prevented or at least reduced by determining analyte concentration as a function of a light scattering pattern arising from precipitate formation, rather than using a conventional colorimetric or fluorometric radiometric detection system relying upon a change in the absorption or emission spectrum of the element to measure analyte concentration.

An element for analysis of multiple analytes also presents the further difficulty of obtaining maximum sensitivity for two or more analytes, one of which may be present at an abnormally low concentration and one other of which at an abnormally high concentration.

For example, in certain pathological conditions such as jaundice, diagnosis often depends upon being able to determine the concentration of one serum analyte, e.g., cholesterol, which may be severely depressed and the concentration of another serum analyte, e.g., bilirubin, which may be highly elevated. When these two analytes are evaluated at these abnormal concentration levels by conventional absorption techniques, however, one obtains a strong signal corresponding to the elevated concentration of the one analyte (which generally leads to high sensitivity), and, unfortunately, a weak signal corresponding to the depressed concentration of the other analyte (which generally leads to low sensitivity).

A single, dry chemistry analytical element capable of multiple analyte detection while retaining the simplicity of conventional absorption or emission detection techniques would be of substantial benefit to the art. Such an element would be particularly desirable if it did not require special barrier means to prevent liquid contact among individual interactive compositions contained in the element (thereby simplifying element manufacture and construction) and could minimize the potential interference problem presented by multiple analytes as well as reduce the difficulty of obtaining good sensitivity for multiple analytes, even though one analyte is present at an abnormally low concentration while another is present at an elevated concentration.

SUMMARY OF THE INVENTION

The present invention features "dry chemistry" analytical elements for the analysis of multiple analytes contained in a liquid test sample. Thus, a single element of the invention provides for the analysis of at least two analytes in a liquid. An element of the invention has an essentially dry matrix permeable to the test liquid and at least a portion of the matrix comprises (a) a first interactive composition for the generation of a first radiometrically detectable species corresponding to the presence and/or concentration of one of the analytes, or a reaction or decomposition product thereof, and (b) a second interactive composition for the inhibition or the destruction of a second radiometrically detectable species corresponding to the presence and/or the concentration of one of the other analytes, or a reaction or decomposition product thereof. (The phrase "inhibition of a radiometrically detectable species" and similar expressions herein refer to inhibiting the production of a detectable species.)

At least one component of each of the aforesaid first and second interactive compositions is positioned within the matrix of the element to be in liquid contact with another. In addition, each of the aforesaid first and second radiometrically detectable species produced within the element is selected to have a different, characteristic, detectable absorption or emission peak in the electromagnetic spectrum.

In accord with certain preferred embodiments, analytical elements of the present invention are carried on a support, preferably a radiation-transmissive support, and other zones such as spreading zones, registration zones, and the like can also be present in the element. In certain especially preferred embodiments, the analytical elements of the present invention are multi-zone elements wherein a portion of at least one of the interactive compositions is contained in one or more reagent zone(s) and these zones (as well as any other zones such as spreading zones, registration zones, and the like) are present as superposed layers carried on a support, each of these layers being in fluid contact with one another.

In the aforementioned preferred embodiment, the reagent zone(s) are typically present in the element interposed between a spreading zone and a registration zone(s). The spreading zone receives an applied liquid sample and uniformly meters it to the interposed reagent zone(s). The radiometrically detectable absorption or emission changes produced in the element in response to the generation or inhibition of detectable species are measured in the registration zone(s) of the element. Other optional zones such as subbing zones to promote interlayer adhesion and radiation-blocking zones to enhance measurement of radiometrically detectable changes occurring in the element can also be present. The configuration of analytical elements having such zones as reagent zones, spreading zones, registration zones, radiation-blocking zones, and subbing zones may be found by reference, for example, to Przybylowicz and Millikan, U.S. Pat. No. 3,992,158 issued Nov. 16, 1976 and Clement, U.S. Pat. No. 4,042,335 issued Aug. 16, 1977.

A further embodiment of the invention provides an improved method for the analysis of multiple analytes contained in an aqueous liquid sample which employs the above-described analytical element. This can be achieved by contacting together the analytical element containing the aforementioned interactive compositions and radiometrically detecting, after a predetermined time, the spectral absorption or emission changes produced in the element in response to the presence and/or concentration of each of the desired analytes.

DESCRIPTION OF THE PREFERRED EMBODIMENTS

An essential feature of the present invention is the selection of the interactive compositions to be used in the analytical element. Each element of the invention must contain at least two such interactive compositions designated herein a first and second interactive composition. (The designations "first" and "second" are merely for purposes of convenience and to avoid confusion. They do not imply any special ordering or arrangement in terms of reactivity, element structure, or the like.) One of these interactive compositions generates a radiometrically detectable species having a characteristic absorption or emission peak, preferably at a wavelength above 300 nm, in an amount corresponding to the presence and/or concentration of one of the analytes, and one of these compositions inhibits or destroys a radiometrically detectable species having a characteristic absorption or emission peak, preferably at a wavelength above 300 nm, in an amount corresponding to the presence and/or concentration of one of the other analytes. In addition, the radiometrically detectable species employed in the element should be selected to have different, characteristic absorption or emission peaks, these peaks preferably (but not necessarily) being separated by at least about 5 nm to facilitate their resolution.

Each of the first and second interactive compositions is located in the element within an essentially dry matrix permeable to the liquid under analysis, and one or more components of each of these compositions are in liquid contact with another. This permits the liquid sample containing the analytes to readily contact a portion of each interactive composition. No special barrier(s) to prevent liquid transport between portions of individual interactive compositions are required in the elements of the invention.

An analytical element containing two or more interactive compositions, one of which generates a detectable species, and at least one other of which inhibits or destroys a detectable species, advantageously provides a resultant element wherein the radiometrically detectable changes produced in the element by each analyte can be selected to provide improved sensitivity. For example, when each of the desired analytes under analysis is present in the test liquid in a relatively low concentration, one can eliminate the problem of attempting to resolve minimum absorption or emission changes for each of the analytes. In addition, when one of the analytes is present in the liquid sample in relatively low concentration and another at a relatively high concentration, the present invention provides a single element capable of providing maximum detectable changes for each of the analytes. This can be achieved by detecting the low concentration analyte with the interactive composition which inhibits or destroys a detectable species and the high concentration analyte with the interactive composition which generates a detectable species. Thus, concentration changes for both the low and high concentration analytes produce maximum changes in the respective detectable species for these analytes.

To further reduce and/or eliminate spectral interference problems, particularly those associated with the analysis of aqueous biological liquids containing proteins, the interactive compositions selected for use in a preferred embodiment of the present element are chosen such that the radiometrically detectable species produced upon interaction of these compositions with their respective analytes, or analyte reaction or decomposition products, have a characteristic absorption or emission peak in a region of the electromagnetic spectrum above 300 nm. This avoids the problem of spectral interference resulting from the characteristic protein absorption band existing in the 200 to 300 nm region of the spectrum. In addition, this feature permits the use of conventional spectrophotometric absorption and emission detection systems.

Specific useful interactive compositions can be widely varied. Compositions which interact with the analyte (or a reaction or decomposition product of such analyte) to produce an amount of a detectable species corresponding directly or inversely to the concentration of such analyte typically produce such detectable species through the release of a performed detectable species contained in the composition or through the formation of a detectable species by the composition. In a preferred embodiment, one employs an interactive composition in a multi-zone element that permits the detectable species which is formed or released to migrate to a separate zone of the element, e.g., a registration zone, for radiometric detection. The change in the absorption or emission characteristics of this zone caused by this migration of the detectable species permits determination of the analyte.

A multi-zone element containing an interactive composition which releases a preformed detectable species for migration from one region of the element, for example, a reagent zone, to another region of the element, for example, another reagent zone or a registration zone, can do so because these zones are in liquid or fluid contact with one another. In this regard, one or more components of one interactive composition should be in liquid contact with one or more components of each of the other interactive compositions. However, each of the individual zones of these multi-zone elements need not be in liquid contact with each other zone, fluid contact being sufficient in certain cases. For example, where gaseous analytes or gaseous analyte reaction products, such as $NH_3$, are generated; liquid contact among each of the zones of the element is not required so long as the gaseous substances can pass in the element through each zone into the adjacent zones with which that zone is in fluid contact. Zones in fluid contact may be separated by an intervening zone, for example, a radiation-blocking zone so that the presence of the preformed detectable species in the reagent zone does not interfere with radiometric detection of results occurring in the registration zone. In such case, the intervening zone(s) are in fluid contact with both the reagent zone and the registration zone.

The terms "fluid contact" and "liquid contact" have reference to fluid or liquid contact under conditions of use of the element. Thus, for example, the invention includes elements which may have two or more zones initially spaced apart but which are brought into fluid or liquid contact at the time of use such as by application of compressive force.

Interaction between a particular interactive composition and the specific analyte (or a reaction or decomposition product of the analyte) which it is designed to detect is used herein to refer to chemical activity, catalytic activity as in the formation of an enzyme-substrate complex, or any other form of chemical or physical interaction that can release, produce, or otherwise provide within the analytical elements of the invention a species that is radiometrically detectable, as described above, and indicative of the presence and/or concentration of the desired analyte.

Although each of the interactive compositions can be a single compound which reacts chemically with the analyte to produce a dye or other detectable product, the term "interactive composition" is employed broadly herein to include multi-component compositions. Thus, the term includes a multi-component composition wherein a first component reacts with the analyte (or analyte decomposition or reaction product), and the reaction product of such reaction then reacts with a second component to produce a further reaction product which exhibits the desired detectable change. Indeed, it is not uncommon for such multi-component interactive compositions to employ three or four reaction steps leading to a final product, which can be related back to the pressure and/or amount of the analyte of interest.

Typical radiometrically detectable species, i.e., species that are detectable by the electromagnetic radiation measuring techniques useful in the present invention, include materials such as pigments and dyes which are detectable by radioactive, fluorimetric, colorimetric, or phosphorimetric techniques, preferably colorimetric or fluorimetric techniques.

A partial listing of representative analytes which can be detected and interactive compositions which can be incorporated in these analytical elements is set forth immediately hereinafter. This listing is illustrative and is not intended to be exhaustive. Accordingly, analytical elements capable of detecting other analytes or containing other interactive compositions, although not expressly mentioned herein, are within the scope of the present invention.

In one embodiment, an analytical element for the analysis of both cholesterol and bilirubin is provided. This element represents a particularly preferred embodiment of the invention because bilirubin is an interferent for many conventional methods for the determination of cholesterol. For example, R. D. Ellefson et. al. in *Fundamentals Of Clinical Chemistry*, N. W. Tietz, Ed., 2nd ed., W. B. Saunders Company, Philadelphia, Penn., p. 507 (1976) report that the Leibermann-Burchard reaction for the determination of cholesterol, when applied directly to serum, will produce a color equivalent to 5-6 mg. of cholesterol in the presence of 1 mg. of bilirubin. Similarly, G. Chan et. al., *Clin. Biochem.*, 9 (2), pp. 96–98 (1976) report that lipemic sera (sera with high cholesterol or triglycerides concentrations), when used in a conventional diazo method for the determination of bilirubin, produce bilirubin values that are about 10 to 20% lower than predicted.

In the case of cholesterol and bilirubin, a particularly useful set of interactive compositions is a β-glucuronidase-glucuronide enzymatic reaction composition for cholesterol and an interactive mordant composition for bilirubin.

The β-glucuronidase-glucuronide enzymatic reaction composition for cholesterol contains the enzyme β-glucuronidase and a glucuronide substrate for the enzyme. The glucuronide substrate contains a radiometrically detectable species or precursor therefor which can be converted to a detectable species. In operation, this enzymatic reaction composition provides a measure of the presence and/or concentration of cholesterol by virtue of the characteristic cholesterol inhibition of the enzymatic action of β-glucuronidase on the glucuronide substrate. The radiometrically detectable species affixed to the glucuronide substrate provides a measure of this cholesterol inhibition effect because this species is released as the glucuronide substrate is enzymatically degraded by the β-glucuronidase. Thus, by radiometrically detecting the amount of detectable species released, one is provided with a measure of the effect of cholesterol inhibition on β-glucuronidase which, in turn, can be related to the presence and/or concentration of cholesterol in the liquid sample. The larger the amount of cholesterol in the sample, the more β-glucuronidase will be inhibited and the smaller will be the amount of released detectable species (or its precursor).

Typical detectable species, or precursors therefor, which may be attached to the glucuronide substrate include, among others, the following:
1. Uridine diphosphate which can be detected fluorimetrically by its emission peak at 320 nm. Its excitation wavelength is at 280 nm.
2. Phenol red which can be detected colorimetrically at its 560 nm absorption peak.
3. Bromophenol blue which can be detected colorimetrically at its 590–600 nm absorption peak.
4. p-nitrophenyl which is converted to p-nitrobenzene upon release from a p-nitrophenyl glucuronide substrate. p-nitrobenzene can be detected colorimetrically at its absorption peak in the 360–400 nm region of the spectrum.
5. Phenophthalein which can be detected colorimetrically at its 540 nm absorption peak.

An interactive mordant composition for bilirubin, upon mordanting bilirubin, provides a radiometrically detectable measure for bilirubin either colorimetrically by producing a 10 nm or larger shift in the 400 nm absorption peak of bilirubin and increasing the molar extinction coefficient of bilirubin by at least 50%, or fluorimetrically by producing a new fluorescence emission peak. Thus, a high concentration of bilirubin produces a correspondingly high absorption peak for the mordanted bilirubin, if measured colorimetrically, or a correspondingly high emission peak for the mordanted bilirubin, if measured fluorimetrically. The absorption peak of mordanted bilirubin as determined colorimetrically typically occurs at about 460 nm and the fluorimetric emission peak of mordanted bilirubin typically occurs at about 480–525 nm.

Typical interactive mordant compositions for bilirubin have one or more binding sites for bilirubin and comprise a hydrophobic organic matrix and at least one charge-bearing cationic group, preferably a quaternary ammonium or phosphonium group. Especially preferred are polymeric interactive mordant compositions having repeating units of formula I below in the polymer chain:

I.

wherein

A represents an organo group and constitutes a portion of a polymer backbone;

Q represents a chemical bond(s) or a chemical group linking $M^\oplus$ to A;

$M^\oplus$ represents a cationic group, preferably a quaternary ammonium or phosphonium group, and $X^\ominus$ represents an acid anion such as a halide ion, for example, chloride or bromide; nitrate; methosulfate; p-toluenesulfonate; etc.

In accord with certain especially useful embodiments of the invention, $M^\oplus$ represents a quaternary ammonium or phosphonium group having Formulas II, or III below:

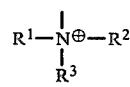
II.

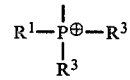
III.

wherein each of $R^1$, $R^2$, and $R^3$, which may be the same or different, represent an aryl, an aralkyl, or an alkaryl group having from 5 to less than about 20 carbon atoms or an alkyl group having from 1 to about 10 carbon atoms.

Preferably, Q, in Formula I represents a hydrocarbon group preferably an arylene, arylenealkylene, alkylenearylene, arylenebisalkylene, or alkylenebisarylene group. Typically, although not required, Q contains from about 5 to about 10 carbon atoms.

As will be appreciated, A in Formula I above can vary depending upon the particular polymeric backbone selected for use. Especially good results, however, have been obtained when A represents an alkylene group. Typically, such alkylene groups contain from 2 to about 10 carbon atoms.

A partial listing of typical polymeric mordant compositions for bilirubin includes the following:

TABLE I

1. Poly(N,N,N-trimethyl-N-vinyl-benzylammonium chloride)
2. Poly[styrene-co-benzyl-(dimethyl)-p-vinylbenzylammonium chloride]
3. Poly(N,N,N-trioctyl-N-vinyl-benzylphosphonium chloride)
4. Poly[styrene-co-(vinylbenzyl)-(trihexyl)-ammonium chloride]
5. Poly(N,N,N-trimethyl-N-vinylbenzylammonium chloride-co-styrene)
6. Poly(styrene-co-N-vinylbenzyl-N-benzyl-N,N-dimethylammonium chloride-co-divinylbenzene)

Further detailed information with respect to the foregoing interactive mordant compositions for bilirubin may be found in Wu and Dappen, U.S. Pat. No. 4,069,017 and Wu and Sullivan, U.S. Ser. No. 932,158, filed Aug. 9, 1978, now U.S. Pat. No. 4,204,839, both of which are incorporated by reference herein.

In addition to the foregoing cholesterol interactive compositions, other analytes capable of detection by interactive compositions that inhibit or destroy production of radiometrically detectable species include:

(i) Detection of blood urea nitrogen (BUN), creatinine, and the like analytes by use of an enzyme which produces ammonia upon interaction with the analyte, the analyte being a substrate for the ammonia-producing enzyme. The amount of ammonia is detected by a radiometric, e.g., colorimetric or fluorimetric, ammonia detection system which destroys an increasing amount of a radiometrically detectable species in response to an increase in $NH_3$ production. An example of one such ammonia detection system is a base bleachable dye, e.g., a styryl type dye as described in Bruschi, U.S. Pat. No. 4,066,403 issued Jan. 3, 1978. For best results, a zone selectively permeable to gas, i.e., $NH_3$, but relatively impermeable to liquid bases can be interposed between the enzyme and the base bleachable dye.

(ii) Detection of bilirubin by use of a competitive binding-displacement interaction between bilirubin and an interactive composition containing a bilirubin-active complex. This complex comprises a diffusible, bilirubin-displaceable, fluorescently-detectable ligand, e.g., 8-anilino-1-naphthalene-sulfonate salt (ANS), bound to a carrier which also can bind bilirubin, the carrier having a greater binding affinity for bilirubin than for the ligand. The ligand fluoresces in its bound state but does not fluoresce in its free state. Thus, when a liquid sample containing bilirubin contacts the bilirubin-active complex, the bilirubin displaces an amount of ANS from the bilirubin-active complex corresponding to the amount of bilirubin in the sample and the resultant decrease in fluorescence of the complex provides a measure of bilirubin. A useful analytical element which employs such a bilirubin active complex is illustrated, for example, in Wu, U.S. Pat. No. 4,069,016 issued Jan. 17, 1978; and the like.

In addition to the foregoing interactive mordant compositions for bilirubin, other analytes capable of detection by interactive compositions that generate the production of a radiometrically detectable species include:

(i) Detection of glucose, cholesterol, lactate, and the like analytes by the use of an appropriate oxidase enzyme, e.g., glucose oxidase, cholesterol oxidase, lactate oxidase, etc., the analyte being a substrate for the oxidase enzyme. The oxidase enzyme produces an amount of hydrogen peroxide that can be detected by a hydrogen peroxide dye generating system. The latter dye generating system typically contains peroxidase and a dye forming composition which, upon oxidation, provides a detectable change in absorption or emission. For example, a glucose detection composition of this type which may be employed in a multi-zone analytical element contains glucose oxidase coupled to a hydrogen peroxide dye-generating composition. One such glucose detection composition is illustrated, for example, in U.S. Pat. No. 3,992,158 noted hereinabove.

(ii) Detection of blood urea nitrogen (BUN), creatinine, and the like analytes by use of an appropriate ammonia-producing enzyme, the analyte being a substrate for the ammonia-producing enzyme. The amount of ammonia is detected by a radiometric, e.g., colorimetric or fluorimetric, ammonia detection system which generates an increasing amount of a radiometrically detectable species in response to an increase in $NH_3$ production. Typical ammonia detection systems include leuco dyes such as leuco cyanine dyes, nitro-substituted leuco dyes, and leuco phthalein dyes—all of which deprotonate from the leuco form to the dye form in the presence of a base such as $NH_3$; and diazonium salts which, in the presence of a color coupler, form a dye in a basic environment such as provided by $NH_3$. A multi-zone analytical element which contains such an ammonia-producing enzyme coupled to an ammonia detection system through a zone selectively permeable to $NH_3$ gas is illustrated, for example, in Bruschi, U.S. Pat. No. 4,066,403;

(iii) Detection of chloride, $Cl^\ominus$, by use of an amylase-dyed starch enzymatic reaction composition. The amount of dye or low molecular weight dyed starch fragment resulting from the degradation of the original dyed starch substrate by the action of amylase produces a radiometrically detectable change that can be related to $Cl^\ominus$ stimulation of amylase activity; and the like.

The amounts of each individual interactive composition and the particular interactive compositions which can be used together in a specific element for multiple analyte detection can be widely varied. As will be appreciated, the amount of a specific interactive composition will vary depending on the specific composition, the analyte it is interactive with, the range of analyte concentration over which the composition is to be indicative, and the amount and type of detectable species to be detected. For any given interactive composition, the optimum amount of the composition to be used can be determined by one of ordinary skill in the art taking into consideration the foregoing factors.

As to particular interactive compositions which can be used together in a given analytical element, one can generally use together any of the foregoing specific interactive compositions which exhibit pH-compatibility and are non-interfering with one another. That is, the individual sequence of interactions to be carried out by each interactive composition should be capable of taking place under similar pH conditions as each of the interactive compositions will typically be in a similar pH environment upon application of a liquid sample to the element. Likewise, because the interactive compositions employed in a specific element will be in liquid contact with one another under conditions of use of the element, the compositions selected for use in a specific element should proceed by analyte interaction mechanisms which do not deleteriously interfere, e.g., cross-react, with one another.

As noted above, the interactive compositions used together in an analytical element of the invention are selected to provide detectable species having different absorption or emission bands. In accord with a preferred embodiment these compositions are further selected so that a first interactive composition generates an increase in the amount of a colorimetrically detectable species in response to a corresponding increase in analyte concentration, and a second interactive composition inhibits or destroys, i.e., decreases, the amount of either a colorimetrically or a fluorimetrically detectable species in response to a corresponding increase in analyte concentration.

An analytical element of the invention typically comprises an initially dry reagent zone containing the above-described interactive compositions. Although not required, an initially dry spreading zone and/or registration zone can also be present in the analytical element so that a preferred analytical element of the invention typically comprises at least two distinct zones which are in fluid contact with one another under conditions of use. Preferably, the various zones are present in an element of the invention as superposed, contiguous layers. Typically, these layers are coated on a support, preferably a radiation-transmissive support. Although preferred analytical elements of the invention are composed of superposed, contiguous layers, other elements may also be prepared in accord with the invention having a different structural arrangement. For example, such an element can have at least two adjacent abutting zones, e.g., a spreading zone and a reagent zone, carried on a support, if necessary or desired, as illustrated in FIG. 2 of U.S. Pat. No. 4,069,017. For purposes of convenience and for illustrating the best mode of the invention, however, the elements of the present invention will hereinafter be described in terms of their structure and characteristics as observed in an integral multilayer, analytical element wherein the different zones are present as superposed, contiguous layers carried on a radiation transmissive support.

An integral element of the invention need only include a reagent layer. However, typically a preferred element also includes a spreading layer and/or a registration layer; the latter layer, if present, preferably being radiation-transmissive. The interactive compositions present in the element are contained in whole or at least in part in the reagent layer. In some cases, each interactive composition is contained in a discrete reagent layer. In other embodiments, one of the interactive compositions (or at least a portion thereof) is contained in the overlying spreading layer or in the underlying registration layer. Such elements can have the layers on a support, preferably radiation-transmissive; however, if the layers demonstrate appropriate durability and integrity, a support is not needed.

In a further embodiment an integral analytical element of this invention can comprise a radiation-transmissive support and (1) one or more reagent layers that are permeable to the multiple analyte-containing liquid sample and that contain an interactive composition as described above, (2) a radiation-blocking layer that is permeable to the detectable species generated or destroyed by the various interactive compositions in response to their respective analytes, and (3) one or more radiation-transmissive registration layers that are also permeable to these detectable species and within which the detectable species can be detected. Optionally, the registration layer can include a mordant for one or more of the detectable species. For example, in that embodiment noted above wherein an interactive mordant composition for bilirubin is used as one of the interactive compositions, this mordant composition can be incorporated in the registration layer, and the resultant layer thus functions as both a registration layer and as a reagent layer. The registration layer is preferably interposed between the support and the radiation-blocking layer, with the radiation-blocking layer interposed between the registration layer and the reagent layer or between the spreading layer and the reagent layer.

The radiation-blocking layer, if present, serves to inhibit passage of electromagnetic radiation, such as at the wavelength or wavelengths used for detection. Using such a layer, color or other potential interferents to result detection can be kept from the registration layer. Such layers include an opacifying agent that, by virtue of its absorbance, reflectance or the like, provides a radiation inhibiting effect when incorporated into the layer. In one aspect, the radiation-blocking layer can include a matrix containing an opacifying agent, such as a pigment like carbon or other inorganic pigment such as a metal salt like titanium dioxide, zinc oxide, barium sulfate, etc. Blushed polymers, which are generally reflective in nature, can comprise the opacifying agent and layers of such blushed polymers as are useful in spreading layers (as described hereinafter) can be used also as radiation-blocking layers. Preferred radiation-blocking layers include an opacifying agent such as a pigment, a polymer in appropriate form, such as a blushed polymer, or both. In one aspect of this embodiment, the permeable matrix of the reagent layer(s), radiation-blocking layer and registration layer are composed of non-fibrous, film-forming natural or synthetic polymers.

In accordance with another preferred embodiment of the present invention, there is provided an integral analytical element with a support having thereon a registration layer, a reagent layer and, optionally, a radiation-blocking layer, all as described above with respect to the foregoing preferred embodiment. Additionally, however, there is included in elements according to this preferred embodiment a spreading layer, desirably isotropically porous and positioned in the element such that the reagent layer is interposed between the registration layer and the spreading layer. In one aspect of this embodiment, all layers are preferably non-fibrous, to enhance quantitative analytical capability of the element. The term "non-fibrous" is used herein with respect to layers and/or materials to indicate that such layers or materials are free or substantially free from fibrous materials, that is, they do not include fibrous components to a degree that would interfere with sample spreading as discussed herein or with detection of the analytical result by radiometric means.

The spreading layer is a layer that can accept a liquid sample, whether applied directly to the spreading layer or provided to it from a layer or layers in fluid contact with the spreading layer. The spreading layer meters and distributes the liquid medium and the analytes of the sample such that a uniform apparent concentration of analytes and liquid are provided at the surface of the spreading layer facing the reagent layer of the element.

As noted above, the layer(s) which contain the interactive compositions described herein have a matrix permeable, preferably uniformly permeable, to the analyte-containing liquid sample. As used herein the term "permeability" includes permeability arising from porosity, ability to swell or any other characteristic. The interactive compositions are distributed, i.e., dissolved or dispersed, in the permeable matrix of these layers. In those cases where the interactive composition(s) is itself film-forming or otherwise readily coatable as a uniform layer or zone, a separate permeable matrix material may not be required. The choice of a matrix material is, of course, variable and dependent on the components to be distributed therein. In any case, the matrix material should be "non-interfering" with respect to the interactive composition(s) and detectable species to be generated or destroyed, i.e., the matrix material should be incapable of deleteriously affecting production or detection of the detectable species by the respective interactive compositions contained in the element.

Matrix materials for reagent layers, as well as registration and radiation-blocking layers, are typically (but not necessarily) non-fibrous and can include non-interfering hydrophilic materials such as gelatin including acid-hydrolyzed gelatins, e.g., pigskin gelatins, or derivatives thereof having an isoelectric point of about 9.1; hydrophilic cellulose derivatives; polysaccharides such as dextran, gum arabic, agarose and the like; and also synthetic substances such as water-soluble polyvinyl compounds like poly(vinyl alcohol) and poly(vinyl pyrrolidone), acrylamide polymers, etc. Non-interfering organophilic materials such as cellulose esters and the like can also be useful. To enhance permeability of these layers, if not porous, it is often useful to employ a matrix material that is swellable in the solvent or dispersion medium of liquid under analysis. Also, it may be necessary to select as a matrix material a material that is compatible with the application of an adjacent layer, such as by coating means, during manufacture of the element. As an example, where the formation of discrete, contiguous layers is desired and the intended analysis will be of aqueous liquids, it may be appropriate to select an essentially water soluble matrix for the reagent layer and essentially organo-soluble or organo-dispersible ingredients for an adjacent layer, such as a spreading layer. In such manner, mutual solvent action is minimized and a clearly delineated layer structure can be formed. In many cases, to prevent diffusion of high molecular weight protein materials into a reagent layer (which materials may be potential interferents for a low molecular analyte such as bilirubin), it may be desirable to have the reagent layer of lower permeability than is the spreading layer itself. This can readily be accomplished by reducing the effective pore size of the reagent layer. Relative permeability or porosity can be determined by well-known techniques.

Although uniform distributions of the interactive compositions within the permeable matrix of the elements are often preferred, they may not be necessary. Interactive compositions soluble in the liquid under analysis may advantageously be immobilized in a reagent layer, particularly when the reagent layer is porous. In a preferred embodiment, the detectable species of an interactive composition is diffusible such that, for example, it can move into an adjacent, permeable registration layer. Such diffusivity can be imparted to detectable species not inherently diffusible by means known to those skilled in chemical synthesis, usually by the addition of chemical groups that impart the desired solubility. Where aqueous liquids are to be analyzed, solubilizing groups such as hydroxyl groups, carboxyl groups, sulfonic acid groups and the like can be useful for purposes of solubilization.

One can also include in a "dry chemistry" analytical element of the invention an appropriate pH buffering composition. The buffering composition can be incorporated in the reagent layer or in one or more of the other layers present in a particular analytical element of the invention to impart to the reagent layer, under conditions of use of the element, a pH effective to enhance or maintain a particular analytical reaction scheme within the element. Representative of specific buffering compositions which can be used are those buffering compositions set forth hereinafter in the Examples as well as others which can provide the desired pH, such as may be described by Good in *Biochemistry*, 5, 467 (1966).

In preparing integral analytical elements of this invention, the layers can be preformed as separate layers which can thereafter be laminated prior to use or maintained as separate layers until brought into fluid contact when the element is in use. However, a convenient procedure which can avoid problems of multiple stripping and lamination steps when contiguous layers are desired, is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well-known in the preparation of light-sensitive photographic films and papers. Any interlayer adhesion problems can be overcome without harmful effect by means of surface treatments including extremely thin application of subbing materials such as are used in photographic films.

For coatable reagent layers, a coating solution or dispersion including the matrix material and incorporated interactive compositions can be prepared, coated as discussed herein and dried to form a dimensionally stable layer. The thickness of any reagent layer and its degree of permeability are widely variable and depend on actual usage. Dry thicknesses of from about 10 microns to about 100 microns have been convenient, although more widely varying thicknesses may be preferable in certain circumstances. Fibrous reagent layers can be formed by impregnation of a fibrous matrix, in accordance with well-known techniques.

The matrix of useful spreading layers can be prepared using a variety of components as described in U.S. Pat. No. 3,992,158. Fibrous and non-fibrous materials may be used although, as described in U.S. Pat. No. 3,992,158, non-fibrous components are highly preferred. Preferred non-fibrous materials include particulate materials, blushed polymer compositions, and mixtures thereof as described in U.S. Pat. No. 3,992,158. Spreading layers can be prepared by coating from solution or dispersion. The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers of from about 50 microns to about 300 microns dry thickness have been particularly useful. However, wider variations in thickness are acceptable and may be desirable for particular elements.

Radiation-blocking layers and registration layers can be prepared using methods and thicknesses as used when preparing coatable reagent layers, but with constituents appropriate for the particular layer. In the case of registration layers, in addition to their permeability and radiation-transmissiveness, they are desirably substantially free from any characteristic that might appear as or contribute to mottle or other noise in the detection of an analytical result produced in an integral element of the invention. For example, any variations in color or in texture within the registration layer, as could occur if fibrous materials, e.g., some papers, are used as a permeable medium, may be disadvantageous due to non-uniform reflectance or transmittance of detecting energy. This is also true regarding layers, e.g., radiation-blocking and reagent layers, of which at least the lower surface would be observable by a detection means examining a radiation-transmissive registration layer. Further details relating to useful registration and radiation-blocking layers can be found in Clement, U.S. Pat. No. 4,042,335, issued Aug. 16, 1977.

The present analytical elements can be self-supporting or carried on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result detection. Preferred supports include radiation-transmissive support materials that transmit electromagnetic radiation of a wavelength or wavelengths within the region between about 200 nm and about 900 nm. For fluorimetric detection of analytical results through the support, it is desirable for the support to transmit over a somewhat wider band than is necessary for non-fluorescence measurements, or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics.

In the layers of the element, it can be advantageous to incorporate one or more surfactant materials such as anionic and nonionic surfactant materials. They can, for example, enhance coatability of layer formulations and enhance the extent and rate of spreading in spreading layers that are not easily wetted by liquid samples in the absence of an aid such as a surfactant. In particular, it can be desirable to incorporate a relatively large amount of a surfactant, such as a non-ionic surfactant, in the spreading layer of the elements of the invention to normalize transport of analytes contained in an aqueous proteinaceous liquid sample in and through this layer of the element. Preferred amounts of surfactant effective to achieve normalized analyte transport are typically between about 1% and about 15% by weight based on the dry weight of the layer. Further details regarding this use of surfactant materials to achieve normalized analyte transport may be found by reference to Goffe et al, U.S. Pat. No. 4,050,898, issued Sept. 27, 1977.

Analytical elements of the present invention can be adapted for use not only in the field of clinical chemistry, but in chemical research and in chemical process control laboratories. They are particularly well suited for use in clinical testing of body fluids, such as blood, blood serum and urine, because in this work a large number of repetitive tests are frequently conducted and test results are often needed a very short time after the sample is taken. In analyzing blood with the analytical element of this invention, the blood cells may first be separated from the serum, by such means as centrifuging, and the serum applied to the element.

A variety of different elements, depending on the analysis of choice, can be prepared in accordance with the present invention. Elements can be configured in such varied forms as elongated tapes of any desired width, sheets or smaller chips.

The preferred multilayer elements are placed in use by applying to the element a sample of liquid under analysis. Typically, a multilayer element will be structured such that an applied sample will contact a spreading layer, if present, prior to the reagent layer and will first contact such spreading layer at its surface furthest removed from such reagent layer. Because analytical accuracy of the present elements is not substantially diminished by variations in the volume of applied samples, especially when a spreading layer is present in the element, sample application by hand or machine is acceptable. For reasons of convenience in detecting an analytical result, however, reasonable consistency in sample volume may be desirable.

In a typical analytical procedure using the present multilayer elements, which would be manual or automated, the element is taken from a supply roll, chip packet or other source and positioned to receive a free drop, contact spot or other form of liquid sample, such as from an appropriate dispenser. After sample application, and desirably after the liquid sample has been taken up by a spreading layer, if present, the element is exposed to any conditioning, such as heating, humidification or the like, that may be desirable to quicken or otherwise facilitate obtaining any test result. If an automated procedure is used, it can also be desirable to have any spreading layer accomplish its function within several seconds, but allowing sufficient time to provide metering.

After the analytical result(s) is obtained as a detectable change, it is measured, usually by passing the element through a zone in which suitable apparatus for reflection, transmission and/or fluorescence spectrophotometry is provided. Such apparatus would serve to direct a beam of light through the support and the registration layer. The light would then be reflected, such as from a radiation-blocking layer or an opaque spreading layer in the element, back to a detecting means or would pass through the element to a detector, in the case of transmission detection. Use of reflection spectrophotometry can be advantageous in some situations as it can effectively avoid interference from residues which may have been left on or in the layers of the element. Conventional techniques of fluorescence spectrophotometry can also be employed if the detectable species is a material which in its free form exhibits an increase or decrease in fluorescence as compared to its fluorescence when bound in an interactive composition. Detection would be accomplished using energy that excites the fluorescent species and a detector that senses its fluorescent emission.

Generally, electromagnetic radiation in the range of from about 300 to about 900 nm has been found useful for measuring detectable changes produced in elements of the invention, although any radiation to which the element is permeable and which is capable of quantifying the detectable change produced in the element can be used. Various calibration techniques can be used to provide a control for the analysis. As one example, a sample of analyte standard solution can be applied adjacent to the area where the drop of sample is placed in order to permit the use of differential measurements in the analysis.

Because the elements of the invention detect multiple analytes, the element can be used to simultaneously detect for each analyte to which the element is sensitive. Thus, a single liquid sample applied to the element can simultaneously be evaluated for each of two or more different analytes. In this mode of operation, two or more detectable changes will be concurrently produced in the element, and appropriate detection systems can be employed to measure each of these changes.

The following examples are presented as a further illustration of the invention. In these Examples the following materials and abbreviations for these materials are employed:

β-glucuronidase—prepared from bovine liver or *E.coli* obtained from Sigma Chemical Company, St. Louis, Mo. Units of β-glucuronidase noted in the following examples are measured by the method of Fishman et al. as described in W. H. Fishman et al., *J. Biological Chemistry*, Vol. 173, 449 (1948).

Mordant A—a polymeric mordant composition comprised of poly[styrene-co-(vinylbenzyl)-(trihexyl)-ammonium chloride] as described in U.S. Pat. No. 4,069,017.

UDP—uridine diphosphate having a fluorescence emission peak at about 320 namometers when excited by 280 namometer wavelength radiation.

UDPQ—uridine diphosphate glucuronide available, for example, from Sigma Chemical Company.

BPB—bromophenol blue having an absorption peak at about 600 nm.

BPBG—bromophenol blue glucuronide prepared in a manner similar to that described by J. A. R. Mead et al., *Biochemical Journal*, Vol. 61, p. 569–574 (1955).

EXAMPLE 1

In this Example an integral multilayer analytical element was prepared. This element had a spreading layer as a top layer superposed on a reagent layer which, in turn, was superposed on a registration layer which, in turn, was carried on a radiation transmissive support composed of a flexible cellulose acetate film bearing a thin adhesive subbing layer to promote bonding of the support to the overlying registration layer. This element was designed to detect for two analytes, bilirubin and cholesterol.

The mechanism employed for bilirubin detection was that described in Wu et al, U.S. Pat. No. 4,069,017 as discussed hereinabove. In this method of bilirubin detection, an interactive mordant composition for bilirubin is employed wich, upon mordanting bilirubin, produces a shift of at least about 10 nanometers in the normal bilirubin absorption peak at 440 namometers and increases the molar extinction coefficient of bilirubin by at least 50 percent. The interactive mordant composition employed in the multilayer element of this example was Mordant A. The absorption peak for bilirubin detection, i.e., the absorption peak of mordanted bilirubin, was at 460 namometers. The non-ionic surfactant, Triton X-100, was employed in the spreading layer of this multilayer element to aid in the dissociation of bilirubin bound to serum protein and to normalize transport of the bilirubin through the spreading layer of this multilayer element. Mordant A employed in this multilayer element was incorporated in the registration layer of the element and represented the sole constituent of this layer, the resulting registration layer having an amount of Mordant A corresponding to a coating coverage of 0.44 g/m$^2$.

The mechanism of cholesterol detection employed in the multilayer element of this example was that discussed hereinabove, namely a β-glucuronidase-glucuronide enzymatic reaction system whereby cholesterol inhibition of β-glucuronidase activity on a glucuronide substrate containing a detectable species is employed as the detection system for cholesterol. In the multilayer element of this example, the glucuronide substrate having a detectable species attached to it was UDPG. As β-glucuronidase acted on UDPG, UDP was cleaved from the glucuronide and migrated into the reagent and registration layers for detection. Free UDP represents a fluorescent species having the above-identified excitation and emission bands.

In the multilayer element of this example, the spreading layer prevented serum protein, e.g., albumin, which could exhibit fluorescence from migrating into the reagent or registration layer and thereby interfering with UDP detection. The UDPG substrate was incorporated in the spreading layer at a coverage of about 0.06 g/m$^2$ and the β-glucuronidase was incorporated in the reagent layer at a coverage of about 3.2 g/m$^2$. The β-glucuronidase employed in the multilayer element of this Example had an activity corresponding to 50,000 units per milligram of protein.

The other components contained in the multilayer element of this Example were as follows: The spreading layer composition, in addition to the presence of Triton X-100 and UDPG, consisted of a non-fibrous, isotropically porous composition containing blushed cellulose acetate at a coverage of about 7 g/m$^2$ and particulate titanium dioxide pigment at a coverage of about 50.0 g/m$^2$. This blushed polymer spreading layer composition was prepared in a manner similar to that described in Example 3 of U.S. Pat. No. 3,992,158. The reagent layer of the multilayer element of this Example, in addition to the glucuronidase discussed above, also contained as a permeable matrix material poly(acrylamide) at a coverage of about 1.08 g/m$^2$.

The β-glucuronidase-glucuronide enzymatic detection system for cholesterol represented one interactive composition contained in the element of this Example, the β-glucuronidase and the UDPG portions of this enzymatic detection system being distributed between the spreading layer and the reagent layer of the element. Mordant A, a polymeric interactive mordant composition for bilirubin, represented the second interactive composition contained in this element, this interactive composition being incorporated in the registration layer of the element.

A series of identical integral multilayer elements having the structure and composition noted above was then used to detect both the cholesterol and bilirubin levels present in a series of aqueous serum-based samples containing different known levels of both cholesterol and bilirubin, the cholesterol levels being detected fluorimetrically and the bilirubin levels being detected colorimetrically. This was accomplished as follows: A 10 microliter droplet of the serum-based sample was spotted onto the spreading layer of an element and a fluorimeter was used to detect for changes in the fluorescence emission exhibited by the element. The fluorimeter directed a beam of exciting light having a wavelength of 280 nm into the element through the transparent cellulose acetate support and the fluorescence emission of the element was monitored at both the excitation wavelength of 280 nm and the emission wavelength of UDP at 320 nm. The changes in fluorescence thus detected by the fluorimeter were measured on a recorder, and the percentage change in fluorescence was computed. Table II below shows the percent change in fluorescence for each different known amount of cholesterol contained in each sample tested. As can be seen in Table II there was a marked decrease in fluorescence as the amount of cholesterol contained in the series of serum-based samples increased. The data in Table II was obtained on the multilayer elements after the 10 microliter droplets had been spotted on the element and allowed to interact with the element for a total time of 5 minutes at 37° C. and 50% relative humidity.

TABLE II

| Percent change in fluorescence | Test sample cholesterol concentration (mg/dl) |
| --- | --- |
| 100 | 0 |
| 95 | 160 |
| 78 | 270 |
| 45 | 400 |

The same multilayer elements used for testing cholesterol concentrations as described immediately hereinabove were then incubated an additional 2 minutes at 37° C. and 50% RH and evaluated colorimetrically to test for bilirubin. The elements were thus incubated for a total of approximately 7 minutes at 37° C. and 50% RH. Thereafter, the reflection density of each element was measured at 460 nm by directing a beam of light through a 460 nm (±10 nm) interference filter into the element through the support and detecting the optical density of the reflected beam of light. The results thus obtained are shown below in Table III. As indicated in Table III an increase in optical density at the 460 nm absorption band of mordanted bilirubin was obtained corresponding to an increase in the amount of bilirubin contained in the serum-based samples spotted onto the multilayer elements.

TABLE III

| 460 nm reflection density of mordanted bilirubin | Test sample bilirubin concentration (mg/dl) |
| --- | --- |
| 0.001 | 0 |
| 0.05 | 1 |
| 0.16 | 5 |
| 0.32 | 19.2 |

As can be seen from the results of the multilayer element described in this example, a single element of the present invention can detect the presence and/or concentration of two or more analytes, such as bilirubin and cholesterol, without substantial interference, even though the interactive compositions for each analyte were in liquid contact with one another during the respective assays for each analyte. As further demonstrated in this Example, the increase in the colorimetric absorption peak for one of the analytes, namely bilirubin, is high when the concentration of this analyte is high, whereas the fluorimetric emission peak for cholesterol is high when the concentration of this analyte is low. This demonstrated feature of the element provides excellent sensitivity for these analytes at concentration ranges of diagnostic significance.

EXAMPLE 2

In this Example a multilayer element similar to that described in Example 1 was prepared, except that the UDPG substrate for $\beta$-glucuronidase employed in the element of Example 1 was replaced by bromophenol blue glucuronide, BPBG. Again, as in Example 1, the glucuronide substrate for $\beta$-glucuronidase, in this case BPBG, was incorporated in the spreading layer of the element. The amount used was 0.05 to 0.1 g/m². The remaining layers and materials contained in these layers of the element of this Example were identical to those described in Example 1, except that the amount of $\beta$-glucuronidase contained in the reagent layer of the element of this Example was approximately one-third as large as that used in Example 1, namely 1.1 g/m². The detection of cholesterol and bilirubin provided by the multilayer element of this example was evaluated in a manner similar to that described in Example 1 hereinabove, except that in this Example a colorimetric detection system for cholesterol was used because BPB was employed as the detectable species in the $\beta$-glucuronidase-glucuronide enzymatic detection system for cholesterol. Measurement of the reflection density exhibited by the element at the 600 nm absorption peak of BPB was accomplished by directing a beam of light through a 600 nm (±10 nm) interference filter into the element through the support and then detecting the reflection density of the reflected beam at 600 nm. The 600 nm absorption peak of bromophenol blue was clearly distinguishable from the 460 nm absorption peak used for the detection of the mordanted bilirubin.

A series of identical multilayer elements were then tested with a series of aqueous serum-based test samples, each of the samples containing a different known amount of cholesterol and a different known amount of bilirubin. These tests were carried out in a manner similar to that described in Example 1, except that, of course, in this case both analytes were detected colorimetrically. Table IV below shows that as the amount of cholesterol in the series of samples tested was increased, a corresponding decrease in the optical absorption of BPB at 600 nm was recorded in the element. Table V shows that as the amount of bilirubin in the test samples increased, there was a corresponding increase in optical density at the 460 nm absorption peak of mordanted bilirubin. Thus, the multi-layer element of this example, like the element of Example 1, represents a useful element for the detection of two or more analytes, namely cholesterol and bilirubin, without substantial interference problems, even though the interactive compositions for each analyte were in liquid contact during the respective assays for each analyte. In this case, both analytes were detected colorimetrically.

TABLE IV

| 600 nm reflection density Of BPB measured at 2 minutes, 37° C., 50 RH | Test sample cholesterol concentration (mg/dl) |
| --- | --- |
| 0.120 | 0 |
| 0.090 | 164 |
| 0.047 | 272 |
| 0.040 | 345 |
| 0.022 | 407 |

TABLE V

| 460 nm reflection density of mordanted bilirubin at 7 minutes, 37° C., 50 RH | Test sample bilirubin concentration (mg/dl) |
| --- | --- |
| 0 | 0 |
| 0.06 | 1 |
| 0.17 | 7 |
| 0.28 | 14 |
| 0.32 | 18 |

The invention has been described in detail with particular reference to certain preferred embodiments thereof, but it will be understood that variations and modifications can be effected within the spirit and scope of the invention.

We claim:

1. An analytical element for the analysis of analytes in a liquid, said element having an essentially dry matrix permeable to said liquid, at least a portion of said matrix comprising
   (a) a first interactive composition for the generation of a first radiometrically detectable species in an amount corresponding to the presence and/or concentration of one analyte, or a reaction or decomposition product thereof, and
   (b) a second interactive composition for the inhibition or the destruction of a second radiometrically detectable species in an amount corresponding to the presence and/or the concentration of a second analyte, or a reaction or decomposition product thereof;
said first and second interactive compositions being in liquid contact with one another within said matrix during use, and each of said first and second radiometrically detectable species having a different characteristic, detectable absorption or emission peak.

2. An analytical element as defined in claim 1 wherein said first radiometrically detectable species is colorimetrically detectable and wherein said second radiometrically detectable species is fluorimetrically detectable, the absorption or emission peak of each of said species being in a region of the electromagnetic spectrum above 300 nm, the respective peaks being separated by at least about 5 nm.

3. An analytical element as defined in claim 1 wherein each of said first and said second radiometrically detectable species are colorimetrically detectable, the absorption peak of each of said species being in a region of the electromagnetic spectrum above 300 nm, the respective peaks being separated by at least about 5 nm.

4. An analytical element as defined in claim 1 wherein each of said first and second radiometrically detectable species are fluorometrically detectable, the emission peak of each of said species being in a region of the electromagnetic spectrum above 300 nm, the respective peaks being separated by at least about 5 nm.

5. An analytical element as defined in claim 1 wherein said first interactive composition comprises a member selected from the group consisting of
   (i) an interactive mordant composition for detection of bilirubin;
   (ii) a composition comprising an oxidase enzyme coupled to a hydrogen peroxide dye generating system, said composition (ii) being for the detection of an analyte representing a substrate for said oxidase enzyme;
   (iii) a composition comprising an ammonia-producing enzyme coupled to a radiometric ammonia detection system which generates an increasing amount of a radiometrically detectable species in response to an increase in ammonia concentration, said composition (iii) being for the detection of an analyte representing a substrate for said ammonia-producing enzyme, and
   (iv) an amylase-dyed starch enzymatic reaction composition for the detection of chloride.

6. An analytical element as defined in claim 1 wherein said second interactive composition comprises a member selected from the group consisting of
   (i) a $\beta$-glucuronidase-glucuronide enzymatic reaction composition for the detection of cholesterol;
   (ii) a composition comprising an ammonia-producing enzyme coupled to a radiometric ammonia detection system which destroys an increasing amount of a radiometrically detectable species in response to an increase in ammonia concentration, said composition (ii) being for the detection of an analyte representing a substrate for said ammonia-producing enzyme; and
   (iii) a bilirubin-active complex for detection of bilirubin; said complex comprising a diffusible, bilirubin-displaceable, fluorescently detectable ligand bound to a carrier which also can bind bilirubin, said carrier having a greater binding affinity for bilirubin than for the ligand.

7. An analytical element as defined in claim 1 wherein said first interactive composition comprises an interactive mordant composition for detection of bilirubin and said second interactive composition comprises a $\beta$-glucuronidase-glucuronide enzymatic reaction composition for the detection of cholesterol.

8. An analytical element as defined in claim 1 wherein said first interactive composition comprises an interactive mordant composition for detection of bilirubin and said second interactive composition comprises a $\beta$-glucuronidase-glucuronide enzymatic reaction composition for the detection of cholesterol, said glucuronide of said enzymatic reaction composition for cholesterol comprising uridine diphosphate glucuronide or bromophenol blue glucuronide.

9. A multi-zone analytical element for the analysis of analytes, in liquid, said element comprising a support bearing a spreading zone and a reagent zone, said zones providing an essentially dry matrix permeable to said liquid, at least a portion of said matrix comprising
   (a) a first interactive composition for the generation of a first radiometrically detectable species in an amount corresponding to the presence and/or concentration of one analyte, or a reaction or decomposition product thereof, and
   (b) a second interactive composition for the inhibition or the destruction of a second radiometrically detectable species in an amount corresponding to the presence and/or the concentration of a second analyte, or a reaction or decomposition product thereof;
said first and second interactive compositions being in liquid contact with one another within said matrix during use, with at least a portion of said interactive compositions contained in said reagent zone, and each of said first and second radiometrically detectable species having a characteristic, detectable absorption or emission peak in a region of the electromagnetic spectrum above 300 nm, the respective peaks being separated by at least about 5 nm.

10. A multilayer analytical element for the analysis of analytes, in liquid, said element comprising a support bearing, in sequential order from said support, superposed registration layer, reagent layer, and spreading layer, said superposed layers providing an essentially dry matrix permeable to said liquid, at least a portion of said matrix comprising
   (a) a first interactive composition for the generation of a first radiometrically detectable species in an amount corresponding to the presence and/or concentration of one analyte, or a reaction or decomposition product thereof, and
   (b) a second interactive composition for the inhibition or the destruction of a second radiometrically detectable species in an amount corresponding to the presence and/or the concentration of a second analyte, or a reaction or decomposition product thereof;

said first and second interactive compositions being in liquid contact with one another within said matrix during use, with at least a portion of one of said interactive compositions contained in said reagent layer, and each of said first and second radiometrically detectable species having a characteristic, detectable absorption or emission peak in a region of the electromagnetic spectrum above 300 nm, the respective peaks being separated by at least about 5 nm.

11. An analytical element as defined in claim 10 wherein said first radiometrically detectable species is colorimetrically detectable and wherein said second radiometrically detectable species is fluorimetrically detectable.

12. An analytical element as defined in claim 10 wherein each of said first and said second radiometrically detectable species are colorimetrically detectable.

13. An analytical element as defined in claim 10 wherein said first interactive composition comprises a member selected from the group consisting of
  (i) an interactive mordant composition for detection of bilirubin;
  (ii) a composition comprising an oxidase enzyme coupled to a hydrogen peroxide dye generating system, said composition (ii) being for the detection of an analyte representing a substrate for said oxidase enzyme;
  (iii) a composition comprising an ammonia-producing enzyme coupled to a radiometric ammonia detection system which generates an increasing amount of a radiometrically detectable species in response to an increase in ammonia concentration, said composition (iii) being for the detection of an analyte representing a substrate for said ammonia-producing enzyme; and
  (iv) an amylase-dyed starch enzymatic reaction composition for the detection of chloride.

14. An analytical element as defined in claim 10 wherein said second interactive composition comprises a member selected from the group consisting of
  (i) a β-glucuronidase-glucuronide enzymatic reaction composition for the detection of cholesterol;
  (ii) a composition comprising an ammonia-producing enzyme coupled to a radiometric ammonia detection system which destroys an increasing amount of a radiometrically detectable species in response to an increase in ammonia concentration, said composition (ii) being for the detection of an analyte representing a substrate for said ammonia-producing enzyme; and
  (iii) a bilirubin-active complex for detection of bilirubin; said complex comprising a diffusible, bilirubin-displaceable, fluorewcently detectable ligand bound to a carrier which also can bind bilirubin, said carrier having a greater binding affinity for bilirubin than for the ligand.

15. An analytical element as defined in claim 10 wherein said first interactive composition comprises an interactive mordant composition for detection of bilirubin and said second interactive composition comprises a β-glucuronidase-glucuronide enzymatic reaction composition for the detection of cholesterol.

16. An analytical element as defined in claim 10 wherein said first interactive composition comprises an interactive mordant composition for detection of bilirubin and said second interactive composition comprises a β-glucuronidase-glucuronide enzymatic reaction composition for the detection of cholesterol, said glucuronide of said enzymatic reaction composition for cholesterol comprising uridine diphosphate glucuronide or bromophenol blue glucuronide.

17. A method for the analysis of analytes in a liquid, said method comprising
  (a) contacting together said liquid an an analytical element having an essentially dry matrix permeable to said liquid, at least a portion of said matrix comprising
    (i) a first interactive composition for the generation of a first radiometrically detectable species in an amount corresponding to the presence and/or concentration of one analyte, or a reaction or decomposition product thereof, and
    (ii) a second interactive composition for the inhibition or the destruction of a second radiometrically detectable species in an amount corresponding to the presence and/or the concentration of a second analyte, or a reaction or decomposition product thereof;

said first and second interactive compositions being in liquid contact with one another within said matrix during use, with at least a portion of one of said interactive compositions contained in said reagent layer, and each of said first and second radiometrically detectable species having a characteristic, detectable absorption or emission peak; and
  (b) radimetrically detecting, after a predetermined time, a separate detectable change occurring in said element in response to the presence and/or concentration of each of said analytes, at least one detectable change being the result of said inhibition or destruction of said second radiometrically detectable species.

* * * * *

UNITED STATES PATENT AND TRADEMARK OFFICE
CERTIFICATE OF CORRECTION

PATENT NO. : 4,274,832

DATED : June 23, 1981

INVENTOR(S) : Wu and Dappen

It is certified that error appears in the above—identified patent and that said Letters Patent is hereby corrected as shown below:

Column 7, line 52, "400" should read --440--. Column 17, line 41, "wich" should read --which--. Column 24, line 3, "fluorewcently" should read --fluorescently--; line 46, "radimetrically" should be --radiometrically.

Signed and Sealed this

Third Day of November 1981

[SEAL]

Attest:

GERALD J. MOSSINGHOFF

Attesting Officer     Commissioner of Patents and Trademarks